United States Patent [19]

Dale

[11] 4,203,169
[45] May 20, 1980

[54] URINE COLLECTION DEVICE

[75] Inventor: Gerald Dale, Chelmsford, England

[73] Assignee: Medeci Developments Limited, London, England

[21] Appl. No.: 942,353

[22] Filed: Sep. 14, 1978

[30] Foreign Application Priority Data

Sep. 14, 1977 [GB] United Kingdom ............... 38418/77

[51] Int. Cl.$^2$ ............................................. A47K 11/00
[52] U.S. Cl. ...................................... 4/144.1; 4/144.2; 73/421 R; 128/767
[58] Field of Search ................... 4/144.1, 144.2, 144.3, 4/144.4, 112, 341, 1; 128/2 F, 275, 295, 767, 349 R; 156/160; 73/421 R

[56] References Cited

U.S. PATENT DOCUMENTS

| 3,346,883 | 10/1967 | Ersek | 4/144.2 X |
|---|---|---|---|
| 3,428,046 | 2/1969 | Remer et al. | 128/349 R |
| 3,499,327 | 3/1970 | Lane, Jr. | 4/144.1 X |
| 3,597,770 | 8/1971 | Jacuzzi | 4/144.2 |
| 3,625,064 | 12/1971 | Hinman, Jr. et al. | 73/421 R |
| 3,635,091 | 1/1972 | Linzer | 73/421 R |
| 3,654,638 | 4/1972 | Nye | 4/112 |
| 3,680,543 | 8/1972 | Cox | 4/144.1 X |
| 3,894,845 | 7/1975 | McDonald | 73/421 R |
| 3,918,433 | 11/1975 | Fuisz | 128/295 X |
| 3,929,412 | 12/1975 | Villari | 4/144.1 X |

FOREIGN PATENT DOCUMENTS 1354001  5/1974  United Kingdom ..................... 4/144.3

*Primary Examiner*—Stuart S. Levy
*Attorney, Agent, or Firm*—Young & Thompson

[57] ABSTRACT

A mid-stream urine collection device comprises a flat open-topped tray-like receptacle having plastics film wrapped around it under tension with edges secured together across the open top of the receptacle by an adhesive which releases the edges when wetted by urine, so that the film then snaps away from the open top, diverting the first part of the urine stream from the receptacle and permitting the mid-stream part to enter.

8 Claims, 4 Drawing Figures

URINE COLLECTION DEVICE

DESCRIPTION

The invention relates to a collection device for collection of urine for test purposes.

For pathological testing, a urine sample is required to be free of the bacteria which collect around the exit to the bladder and in the uninary passages. These bacteria are swept away by the first part of a urine stream, which must therefore be excluded from the sample to be tested. The remaining part of the stream only, the so-called mid-stream portion, has to be collected. The taking of a mid-stream sample involves a certain amount of explanation even to a normal patient and taking such a sample from a patient who is mentally disturbed can be very difficult and costly in terms of nursing time.

The invention is therefore concerned with the provision of a urine collection device for collection of a mid-stream sample, which device operates, automatically, with minimal co-operation of the patient.

The invention accordingly provides a mid-stream urine collection device comprising an apertured receptacle and closure means initially closing the aperture against admission of urine, in which a mid-stream urine collection device comprising an apertured receptacle and closure means initially closing the aperture against admission of urine, in which the closure means is arranged to divert from the receptacle the first portion of a stream or urine to impinge on the closure means and to be responsive thereto to open the aperture for admission of the remainder of the urine stream.

Preferably the closure means comprises sheet material having adjoining edges held together by adhesive which loses its adhesive properties when wetted by urine, the sheet material being secured to the receptacle to extend across the aperture under tension with the adjoining edges within the area of the aperture. The sheet material, which conveniently comprises plastics film, is advantageously wrapped around the receptacle, which may have the form of a flat tray of aluminium foil, to seal it.

Use of the device in a toilet can be facilitated by the provision of means for mounting the device within the toilet bowl, such means conveniently comprising flexible self-adhesive strips.

The advantages of the invention are to be seen primarily in the speed and ease with which a mid-stream urine sample can be obtained by use of a collection device embodying it.

By way of illustration, the invention is further explained below with reference to the accompanying schematic drawing, in which.

Figure 1:
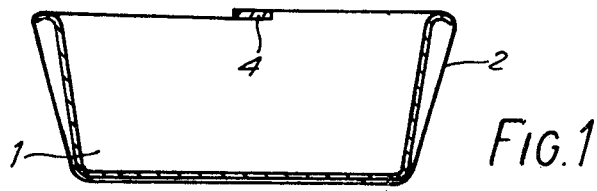
FIG. 1 is a sectional side view of a mid-stream urine collection device embodying the invention in the initial closed condition.

The mid-stream urine collection device of FIG. 1 comprises a receptacle 1 for the urine sample, the receptacle consisting of a flat open-top dish or tray of square or rectangular shape and preferably made of disposable material for example aluminium foil. Associated with the receptacle are means initially closing the open top but responsive to the reception of a stream of urine to open the receptacle and simultaneously to divert away the initial portion of the stream by which the opening is effected. The illustrated closure means comprise springy sheet material 2 stretched from opposed edges at the boundary of the open top of the receptacle 1 to a join within the area of the open top. The sheet material can be polyester or similar plastics film, for example. The sheet material can be secured at the edges of the open top in any suitable way, as by adhesive, but conveniently a single piece of the sheet material is wrapped under tension right around the receptacle, so as to serve as a complete outer cover.

Figure 2:
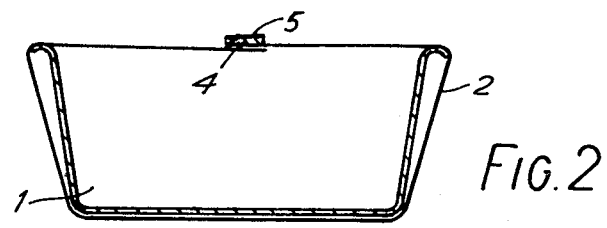
FIG. 2 is a like view of a modified device according to the invention.

The ends of the sheet material 2 are secured together across the open top of the receptacle 1, preferably centrally, by means of an adhesive layer 4 which is water soluble or which otherwise loses its adhesion when wetted by urine. The adhesive of the layer 4 is shown in FIG. 1 as between overlapping portions of the sheet material 2 directly. Instead, as shown in FIG. 2, the adhesive 4 may be carried on a separate closure member or tab 5 in the form of a strip spanning the adjacent edges of the sheet material 2 which then need not overlap. The sheet material 2 can seal at least the interior of the receptacle 1 within it but the collection device can be presented as a sealed and sterilized package in a polythene bag for example without great expense; it is readily disposed of after use.

Figure 3:
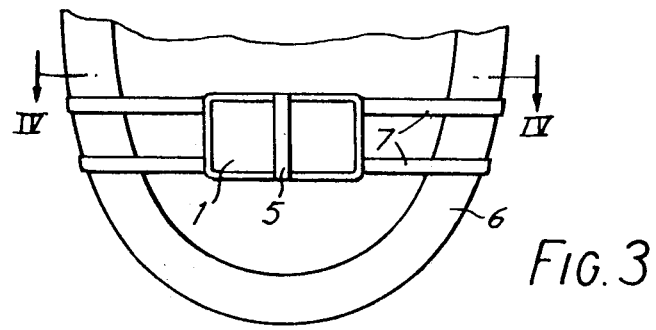
FIG. 3 is a partial schematic plan view of toilet bowl with the device of FIG. 2 positioned for use therein.
Figure 4:
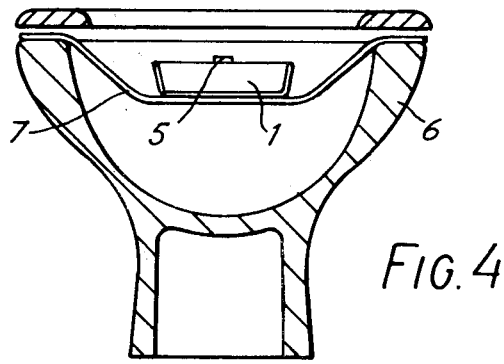
FIG. 4 is a sectional view on the line IV—IV of FIG. 3.

As shown in FIGS. 3 and 4, the collection device may be positioned for use in a toilet bowl 6 by mounting means which are usable also on a commode bowl or bed pan. The illustrated mounting means comprise two flexible self-adhesive straps 7 secured at the middle of their lengths to extend along the underside of the collection device. The ends of the straps are secured for use to the edges of the bowl 6 so as to extend across it, with the collection device positioned centrally. The length of the straps 7 and the weight of the collection device causes the latter to be located below the level of the edges of the bowl 6 in a suitable position for use as shown.

Instead of the flexible straps 7 a rigid reusable member can be employed to rest on the toilet bowl edges and carry the collector on a central depressed portion.

In use, the area in which the edges of sheet material 2 are secured together receives a stream of urine which renders the adhesive ineffective to hold the sheet material edges together. The tension under which the sheet material edges are held together causes the edges to fly apart, so as to divert the urine already present on the upper surface of the sheet material away from the open top of the receptacle and at the same time allow the remainder of the urine stream to be caught within the receptacle. The receptacle thus receives only the desired mid-stream sample with the end-stream, and can be lifted away from the sheet material for subsequent tests.

The collection device can be employed in conjunction with a moisture sensitive alarm, for example a battery powered instrument secured to a belt worn by the patient or placed in any other convenient location, to given an immediate signal that a specimen has been collected.

It will be evident that the present invention can be embodied in various ways other than as specifically described. In the simple collection device illustrated, the initial portion of the stream is diverted away from the receptacle by movement of the closure means under generally horizontal tension, but for example the closure means could instead be arranged to be biassed upwardly, and the initial portion of the urine stream could be diverted to a subsidiary receptacle provided in the device.

I claim:

1. A mid-stream urine collection device comprising:

receptacle means having an interior and edge means surrounding an aperture communicating with said interior, resilient sheet material covering said aperture and having two edge portions, urine soluble adhesive adhesively connecting together said two edge portions, said adhesive means being adapted to release said edge portions when wetted with urine, and means securing said sheet material to said receptacle means so as to close said aperture, said sheet material extending over said aperture under tension and around said edge means in the direction toward the bottom of said receptacle means, with said edge portions within the area of said aperture, whereby when said edge portions separate in response to impingement of urine on said adhesive means said sheet material moves to open said aperture away from said receptacle means interior, thereby diverting therefrom urine previously received on said sheet material.

2. The mid-stream collection device of claim 1 wherein said securing means comprises a portion of said sheet material extending around said receptacle means.

3. The mid-stream collection device of claim 1 wherein said edge portions overlap and said adhesive means comprises a layer of adhesive between said overlapped portions.

4. The mid-stream collection device of claim 1 wherein said adhesive means comprises a closure strip, and an adhesive between said closure strip and said edge portions.

5. The mid-stream collection device of claim 1 wherein said receptacle means has the form of a flat tray.

6. The mid-stream collection device of claim 5 further comprising strap means, means securing said strap means at the central region thereof underneath said flat tray receptacle means, and means at the ends of said strap means for mounting said device within a toilet bowl.

7. the mid-stream collection device of claim 1 wherein said sheet material comprises plastic film material.

8. The mid-stream collection device of claim 1 further comprising self-adhesive means adapted to mount said device within a toilet bowl.

* * * * *